(12) United States Patent
Okamoto et al.

(10) Patent No.: US 10,788,444 B2
(45) Date of Patent: Sep. 29, 2020

(54) GAS SENSOR

(71) Applicant: NGK INSULATORS, LTD., Nagoya-shi, Aichi (JP)

(72) Inventors: Taku Okamoto, Nagoya (JP);
Nobuhiko Mori, Nagoya (JP);
Takayuki Sekiya, Nisshin (JP)

(73) Assignee: NGK INSULATORS, LTD., Nagoya (JP)

( * ) Notice: Subject to any disclaimer, the term of this patent is extended or adjusted under 35 U.S.C. 154(b) by 262 days.

(21) Appl. No.: 15/697,952

(22) Filed: Sep. 7, 2017

(65) Prior Publication Data
US 2018/0074009 A1 Mar. 15, 2018

(30) Foreign Application Priority Data

Sep. 9, 2016 (JP) .................. 2016-176224

(51) Int. Cl.
*G01N 27/41* (2006.01)
*G01N 27/407* (2006.01)
(Continued)

(52) U.S. Cl.
CPC ..... *G01N 27/4071* (2013.01); *G01N 27/4074* (2013.01); *G01N 27/4075* (2013.01); *G01N 27/4076* (2013.01); *G01N 27/419* (2013.01); *G01N 33/0037* (2013.01); *G01N 33/0054* (2013.01); *Y02A 50/245* (2018.01); *Y02A 50/246* (2018.01)

(58) Field of Classification Search
CPC ........... G01N 27/4071; G01N 27/4074; G01N 27/4075; G01N 27/4076; G01N 27/419; G01N 33/0037; G01N 33/0054; Y02A 50/245; Y02A 50/246
USPC ........................................ 204/431
See application file for complete search history.

(56) References Cited

U.S. PATENT DOCUMENTS 8,103,458 B2 * 1/2012 Wang ................. G01N 27/4074
702/24
9,658,133 B2 5/2017 Kaimoto et al.
(Continued)

FOREIGN PATENT DOCUMENTS

JP 5209401 B2 6/2013
JP 5215500 B2 6/2013
(Continued)

*Primary Examiner* — Thanh Truc Trinh
(74) *Attorney, Agent, or Firm* — Mattingly & Malur, PC

(57) ABSTRACT

A sensor element includes a NOx sensor part, a $NH_3$ gas sensor part, and a single common electrode shared by the both parts. The former has a pump cell including a measurement electrode facing an internal space, a pump electrode formed on a surface of the element, and a solid electrolyte therebetween. The latter includes a sensing electrode formed on a surface of the element and having catalytic activity inactivated for a $NH_3$ gas. The common electrode is located to be in contact with a reference gas. The NOx concentration is determined based on a potential difference occurring between the sensing electrode and the common electrode, and a current flowing through the pump cell in a state of controlling a voltage applied across the electrodes to maintain a potential difference between the measurement electrode and the common electrode constant.

21 Claims, 4 Drawing Sheets

(51) Int. Cl.
*G01N 27/419* (2006.01)
*G01N 33/00* (2006.01)

(56) References Cited

U.S. PATENT DOCUMENTS

| | | | | |
|---|---|---|---|---|
| 2009/0014330 | A1* | 1/2009 | Sugaya | G01N 27/4075 204/424 |
| 2011/0048970 | A1* | 3/2011 | Sugaya | G01N 27/419 205/781 |
| 2011/0186431 | A1* | 8/2011 | Horisaka | G01N 27/4075 204/424 |
| 2012/0145543 | A1 | 6/2012 | Sugaya et al. | |

FOREIGN PATENT DOCUMENTS

| | | |
|---|---|---|
| JP | 5416686 B2 | 2/2014 |
| JP | 2015-034814 A | 2/2015 |
| JP | 5745455 B2 | 7/2015 |

* cited by examiner

F I G . 3
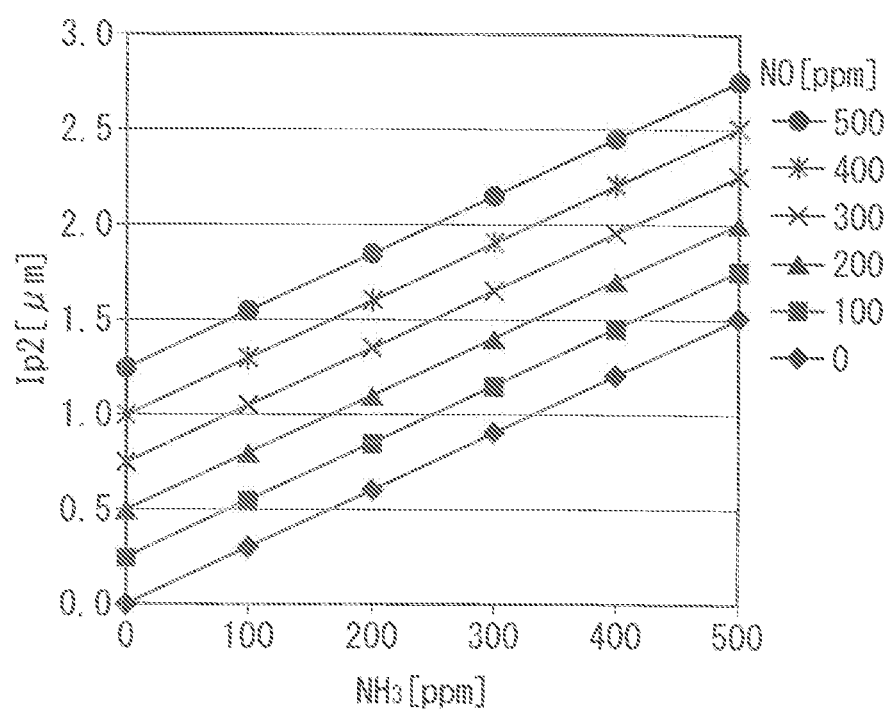

F I G . 4
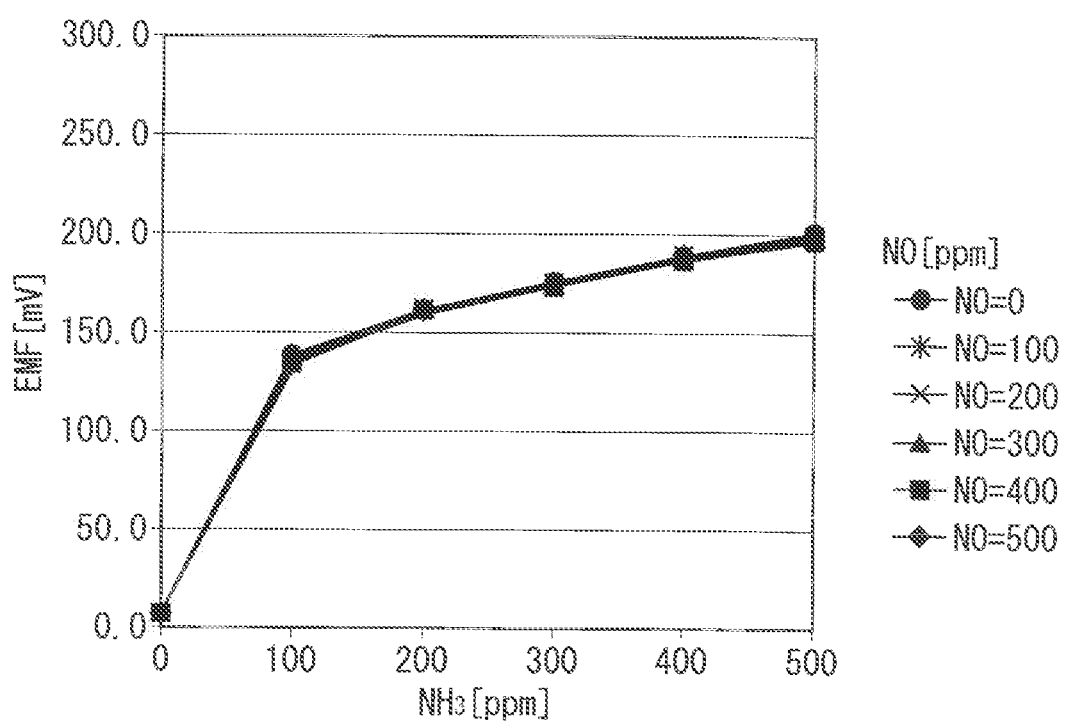

GAS SENSOR

BACKGROUND OF THE INVENTION

Field of the Invention

The present invention relates to a gas sensor for detecting a predetermined gas component in a measurement gas, and, in particular, to a gas sensor capable of determining a NOx concentration.

Description of the Background Art

Various gas sensors have been used to obtain the concentration of a desired gas component in a measurement gas. For example, as an apparatus for measuring a NOx concentration in a measurement gas, such as a combustion gas, a NOx sensor including a sensor element formed of an oxygen-ion conductive solid electrolyte, such as zirconia ($ZrO_2$), is known, and a multi-sensor capable of performing measurement of an ammonia ($NH_3$) concentration in addition to measurement of the NOx concentration is already known (see, for example, Japanese Patent No. 5209401, Japanese Patent No. 5416686, Japanese Patent No. 5745455, Japanese Patent No. 5215500, and Japanese Patent Application Laid-Open Publication No. 2015-034814).

Multi-gas sensors disclosed in Japanese Patent No. 5209401, Japanese Patent No. 5416686, Japanese Patent No. 5745455, Japanese Patent No. 5215500, and Japanese Patent Application Laid-Open Publication No. 2015-034814 each include a NOx sensor part for sensing NOx and an ammonia sensor part for sensing ammonia independently of each other. In view of the effect of an ammonia gas on the result of measurement performed by the NOx sensor part, the result of measurement performed by the NOx sensor part is corrected based on the result of measurement performed by the ammonia sensor part to ensure precision in measuring the NOx concentration.

In the gas sensors disclosed in Japanese Patent No. 5209401, Japanese Patent No. 5416686, Japanese Patent No. 5745455, Japanese Patent No. 5215500, and Japanese Patent Application Laid-Open Publication No. 2015-034814, however, electrodes included in each of the sensor parts and lead wires connecting the electrodes to the outside are independently provided. Accordingly, such sensors have constraints on the layout of the electrodes and routing of wiring, and have little freedom of element design.

The multi-gas sensors disclosed in Japanese Patent No. 5209401, Japanese Patent No. 5416686, Japanese Patent No. 5745455, Japanese Patent No. 5215500, and Japanese Patent Application Laid-Open Publication No. 2015-034814 each include a lamination of alternating solid electrolyte layers and insulating layers, and include the ammonia sensor part located on an insulating layer serving as an outer surface of the sensor element. A pair of electrodes for sensing the ammonia gas is thus located on the insulating layer to be in contact with the measurement gas.

That is, this layout is adopted in a gas sensor including the ammonia sensor part that senses ammonia based on a potential difference occurring between the pair of electrodes, as in the gas sensor disclosed in Japanese Patent No. 5416686, and, in this case, a reference electrode providing a reference potential is exposed to the measurement gas, and thus the reference potential varies due to the effect of variation of an oxygen concentration in the measurement gas. On the other hand, a reference electrode of the NOx sensor part is located inside the sensor element, and thus the stability of measurement of an ammonia gas concentration can be lower than the stability of measurement of the NOx concentration. As a result, the NOx concentration might not suitably be corrected.

SUMMARY

The present invention relates to a gas sensor for detecting a predetermined gas component in a measurement gas, and is directed, in particular, to a gas sensor capable of determining a NOx concentration.

According to the present invention, a gas sensor for detecting a predetermined gas component in a measurement gas includes a sensor element including a lamination of a plurality of oxygen-ion conductive solid electrolyte layers. The sensor element includes: a NOx sensor part; a $NH_3$ gas sensor part; and a single common reference electrode shared by the NOx sensor part and the $NH_3$ gas sensor part. The NOx sensor part includes: at least one internal space into which the measurement gas is introduced from an external space; a NOx measurement electrode formed to face the at least one internal space; and an outer pump electrode formed on a surface of the sensor element, and has a measurement pump cell that is an electrochemical pump cell constituted by the NOx measurement electrode, the outer pump electrode, and a solid electrolyte between the NOx measurement electrode and the outer pump electrode. The $NH_3$ gas sensor part includes a $NH_3$ sensing electrode formed on a surface of the sensor element and having catalytic activity inactivated for a $NH_3$ gas. The single common reference electrode is located between two of the plurality of oxygen-ion conductive solid electrolyte layers to be in contact with a reference gas. The $NH_3$ sensing electrode, the common reference electrode, and a solid electrolyte between the $NH_3$ sensing electrode and the common reference electrode constitute a mixed potential cell. The gas sensor is configured to determine a NOx concentration in the measurement gas based on: a potential difference occurring between the $NH_3$ sensing electrode and the common reference electrode in the mixed potential cell; and a pump current flowing between the NOx measurement electrode and the outer pump electrode in a state of controlling a voltage applied across the NOx measurement electrode and the outer pump electrode to maintain a potential difference between the NOx measurement electrode and the common reference electrode constant.

According to the present invention, the gas sensor can obtain the NOx concentration with stability and high precision even when NOx and a $NH_3$ gas coexist in the measurement gas. In addition, the gas sensor can have simplified configuration compared with a conventional multi-gas sensor.

The gas sensor is preferably configured to determine a $NH_3$ gas concentration in the measurement gas based on the potential difference occurring between the $NH_3$ sensing electrode and the common reference electrode in the mixed potential cell.

In this case, the $NH_3$ gas concentration can concurrently be obtained with high precision and stability.

An object of the present invention is to provide a gas sensor having simpler configuration than a conventional multi-gas sensor, and being capable of obtaining the NOx concentration with stability and high precision in the presence of ammonia.

These and other objects, features, aspects and advantages of the present invention will become more apparent from the

BRIEF DESCRIPTION OF THE DRAWINGS

FIG. 3 illustrates gas concentration dependence of a pump current Ip2 when a $NH_3$ gas and NOx coexist; and FIG. 4 illustrates gas concentration dependence of a potential difference EMF when the $NH_3$ gas and NOx coexist.

DESCRIPTION OF THE PREFERRED EMBODIMENTS

<Schematic Configuration of Gas Sensor>

Figure 1:
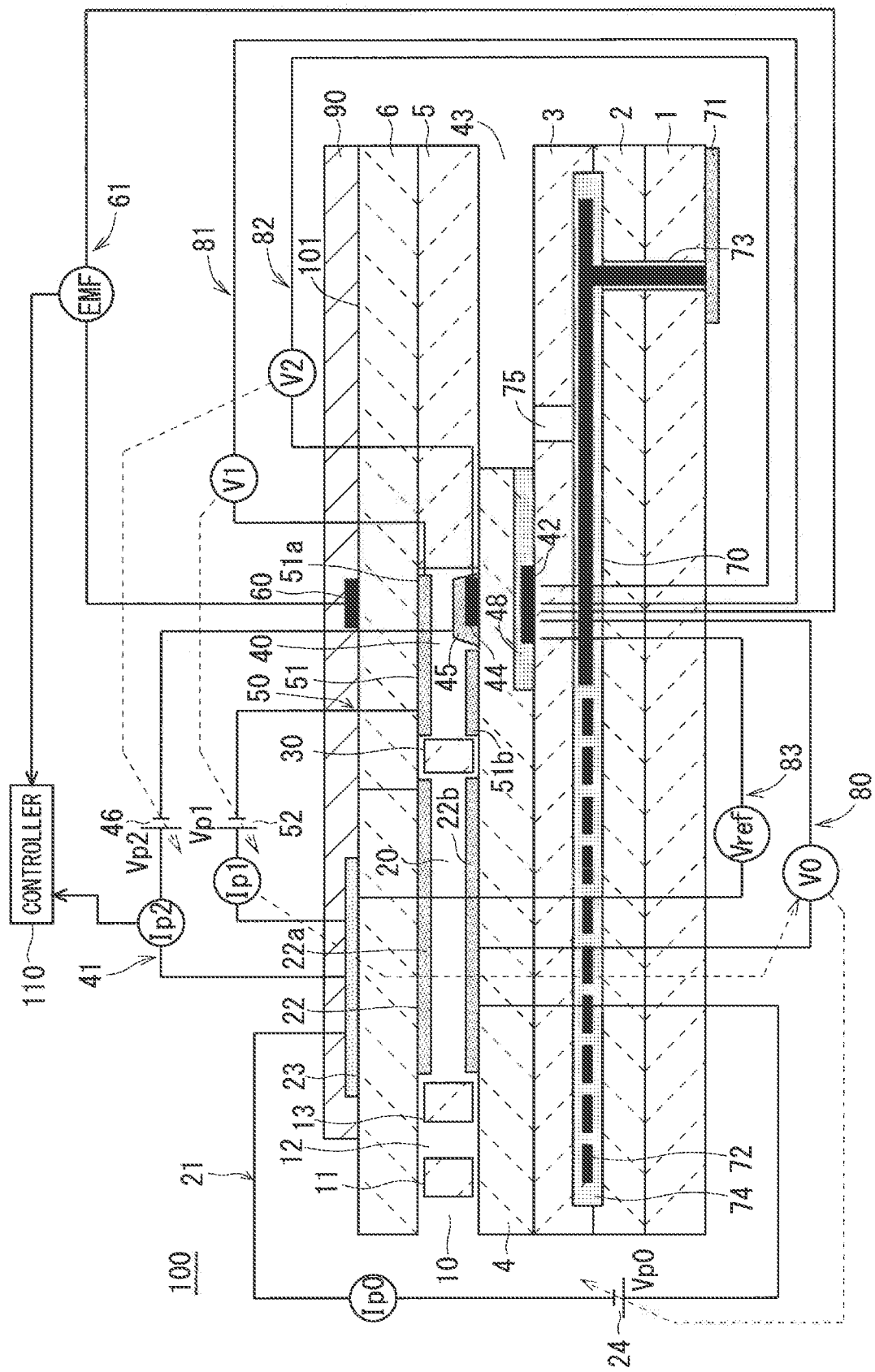
FIG. 1 schematically shows an example of the configuration of a gas sensor 100.

Schematic configuration of a gas sensor 100 according to the present embodiment will be described. FIG. 1 schematically shows an example of the configuration of the gas sensor 100 including a vertical sectional view taken along the longitudinal direction of a sensor element 101, which is a main component of the gas sensor 100. The sensor element 101 has a structure in which six layers, namely, a first substrate layer 1, a second substrate layer 2, a third substrate layer 3, a first solid electrolyte layer 4, a spacer layer 5, and a second solid electrolyte layer 6, each being an oxygen-ion conductive solid electrolyte layer formed, for example, of zirconia ($ZrO_2$), are laminated in the stated order from the bottom side of FIG. 1. Solid electrolytes forming these six layers are dense and airtight. The sensor element 101 is manufactured, for example, by performing predetermined machining and printing of circuit patterns with respect to ceramic green sheets corresponding to respective layers, then laminating these green sheets, and further firing the laminated green sheets for integration.

Between a lower surface of the second solid electrolyte layer 6 and an upper surface of the first solid electrolyte layer 4 at one end portion of the sensor element 101, a gas inlet 10, a first diffusion control part 11, a buffer space 12, a second diffusion control part 13, a first internal space 20, a third diffusion control part 30, and a second internal space 40 are formed adjacent to each other to communicate in the stated order.

The gas inlet 10, the buffer space 12, the first internal space 20, and the second internal space 40 are spaces inside the sensor element 101 that look as if they were provided by hollowing out the spacer layer 5, and that have an upper portion, a lower portion, and a side portion respectively defined by the lower surface of the second solid electrolyte layer 6, the upper surface of the first solid electrolyte layer 4, and a side surface of the spacer layer 5.

The first diffusion control part 11, the second diffusion control part 13, and the third diffusion control part 30 are each provided as two horizontally long slits (openings whose longitudinal direction is a direction perpendicular to the plane of FIG. 1). A part extending from the gas inlet 10 to the second internal space 40 is also referred to as a gas distribution part.

At a location farther from the end portion than the gas distribution part is, a reference gas introduction space 43 having a side portion defined by a side surface of the first solid electrolyte layer 4 is provided between an upper surface of the third substrate layer 3 and a lower surface of the spacer layer 5. Atmospheric air is introduced as a reference gas into the reference gas introduction space 43.

An atmospheric air introduction layer 48 is a layer formed of porous alumina, and the atmospheric air as the reference gas is introduced into the atmospheric air introduction layer 48 through the reference gas introduction space 43. The atmospheric air introduction layer 48 is formed to cover a reference electrode 42.

The reference electrode 42 is an electrode formed to be sandwiched between the upper surface of the third substrate layer 3 and the first solid electrolyte layer 4, and the atmospheric air introduction layer 48 leading to the reference gas introduction space 43 is provided around the reference electrode 42, as described above. As will be described below, an oxygen concentration (oxygen partial pressure) in the first internal space 20 and the second internal space 40 can be measured using the reference electrode 42.

In the gas distribution part, the gas inlet 10 opens to an external space, and a measurement gas is taken from the external space into the sensor element 101 through the gas inlet 10.

The first diffusion control part 11 is a part providing a predetermined diffusion resistance to the measurement gas taken through the gas inlet 10.

The buffer space 12 is a space provided to guide the measurement gas introduced from the first diffusion control part 11 to the second diffusion control part 13.

The second diffusion control part 13 is a part providing a predetermined diffusion resistance to the measurement gas introduced from the buffer space 12 into the first internal space 20.

When the measurement gas is introduced from the outside of the sensor element 101 into the first internal space 20, the measurement gas, which is abruptly taken into the sensor element 101 through the gas inlet 10 due to pressure fluctuation of the measurement gas in the external space (pulsation of exhaust pressure in a case where the measurement gas is an exhaust gas of an automobile), is not directly introduced into the first internal space 20, but introduced into the first internal space 20 after the concentration fluctuation of the measurement gas is canceled through the first diffusion control part 11, the buffer space 12, and the second diffusion control part 13. This makes the concentration fluctuation of the measurement gas introduced into the first internal space 20 almost negligible.

The first internal space 20 is provided as a space used to adjust oxygen partial pressure in the measurement gas introduced through the second diffusion control part 13. The oxygen partial pressure is adjusted by operation of a main pump cell 21.

The main pump cell 21 is an electrochemical pump cell constituted by an inner pump electrode 22, an outer pump electrode 23, and the second solid electrolyte layer 6 sandwiched between the inner pump electrode 22 and the outer pump electrode 23. The inner pump electrode 22 has a ceiling electrode portion 22a that is provided substantially on the entire lower surface of a portion of the second solid electrolyte layer 6 facing the first internal space 20. The outer pump electrode 23 is provided in a region, on an upper surface of the second solid electrolyte layer 6, corresponding to the ceiling electrode portion 22a so as to be exposed to the external space.

The inner pump electrode 22 is formed over upper and lower solid electrolyte layers (the second solid electrolyte layer 6 and the first solid electrolyte layer 4) that define the first internal space 20, and the spacer layer 5 that provides a side wall to the first internal space 20. Specifically, the ceiling electrode portion 22a is formed on the lower surface of the second solid electrolyte layer 6, which provides a ceiling surface to the first internal space 20, a bottom electrode portion 22b is formed on the upper surface of the first solid electrolyte layer 4, which provides a bottom surface to the first internal space 20, and a side electrode portion (not illustrated) is formed on a side wall surface (internal surface) of the spacer layer 5 that forms opposite side wall portions of the first internal space 20 to connect the ceiling electrode portion 22a and the bottom electrode portion 22b. The inner pump electrode 22 is thus provided in the form of a tunnel at a location where the side electrode portion is provided.

The inner pump electrode 22 and the outer pump electrode 23 are each formed as a porous cermet electrode (e.g., a cermet electrode formed of $ZrO_2$ and Pt that contains Au of 1%). The inner pump electrode 22 to be in contact with the measurement gas is formed using a material having a weakened reducing ability with respect to a NOx component in the measurement gas.

The main pump cell 21 can pump out oxygen in the first internal space 20 to the external space or pump in oxygen in the external space to the first internal space 20 by applying, using a variable power supply 24, a desired pump voltage Vp0 across the inner pump electrode 22 and the outer pump electrode 23 to allow a pump current Ip0 to flow between the inner pump electrode 22 and the outer pump electrode 23 in a positive or negative direction.

To detect an oxygen concentration (oxygen partial pressure) in the atmosphere in the first internal space 20, the inner pump electrode 22, the second solid electrolyte layer 6, the spacer layer 5, the first solid electrolyte layer 4, the third substrate layer 3, and the reference electrode 42 constitute an electrochemical sensor cell, namely, a main-pump-control oxygen-partial-pressure detection sensor cell 80.

The oxygen concentration (oxygen partial pressure) in the first internal space 20 can be obtained by measuring electromotive force V0 in the main-pump-control oxygen-partial-pressure detection sensor cell 80.

Furthermore, the pump current Ip0 is controlled by performing feedback control of the voltage Vp0 so that the electromotive force V0 is maintained constant. The oxygen concentration in the first internal space 20 is thereby maintained to have a predetermined constant value.

The third diffusion control part 30 is a part providing a predetermined diffusion resistance to the measurement gas having an oxygen concentration (oxygen partial pressure) controlled by the operation of the main pump cell 21 in the first internal space 20, and guiding the measurement gas to the second internal space 40.

The second internal space 40 is provided as a space to perform processing concerning determination of a nitrogen oxide (NOx) concentration in the measurement gas introduced through the third diffusion control part 30. The NOx concentration is determined, mainly in the second internal space 40 in which an oxygen concentration has been adjusted by an auxiliary pump cell 50, by the operation of a measurement pump cell 41.

After the oxygen concentration (oxygen partial pressure) is adjusted in advance in the first internal space 20, the auxiliary pump cell 50 further adjusts the oxygen partial pressure of the measurement gas introduced through the third diffusion control part in the second internal space 40. Owing to such adjustment, the oxygen concentration in the second internal space 40 can be maintained constant with high precision, and thus the gas sensor 100 is enabled to determine the NOx concentration with high precision.

The auxiliary pump cell 50 is an auxiliary electrochemical pump cell constituted by an auxiliary pump electrode 51, the outer pump electrode 23 (not limited to the outer pump electrode 23 but may be any appropriate electrode outside the sensor element 101), and the second solid electrolyte layer 6. The auxiliary pump electrode 51 has a ceiling electrode portion 51a that is provided substantially on the entire lower surface of a portion of the second solid electrolyte layer 6 facing the second internal space 40.

The auxiliary pump electrode 51 is provided in the second internal space 40 in the form of a tunnel, as with the inner pump electrode 22 provided in the first internal space 20 described previously. That is to say, the ceiling electrode portion 51a is formed on the second solid electrolyte layer 6, which provides a ceiling surface to the second internal space 40, a bottom electrode portion 51b is formed on the first solid electrolyte layer 4, which provides a bottom surface to the second internal space 40, and a side electrode portion (not illustrated) that connects the ceiling electrode portion 51a and the bottom electrode portion 51b is formed on opposite wall surfaces of the spacer layer 5, which provides a side wall to the second internal space 40. The auxiliary pump electrode 51 is thus provided in the form of a tunnel.

As with the inner pump electrode 22, the auxiliary pump electrode 51 is formed using a material having a weakened reducing ability with respect to a NOx component in the measurement gas.

The auxiliary pump cell 50 can pump out oxygen in the atmosphere existing in the second internal space 40 to the external space or pump in oxygen existing in the external space to the second internal space 40 by applying a desired voltage Vp1 across the auxiliary pump electrode 51 and the outer pump electrode 23.

In order to control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an auxiliary-pump-control oxygen-partial-pressure detection sensor cell 81.

The auxiliary pump cell 50 performs pumping using a variable power supply 52 whose voltage is controlled based on electromotive force V1 detected by the auxiliary-pump-control oxygen-partial-pressure detection sensor cell 81. The oxygen partial pressure in the atmosphere in the second internal space 40 is thereby controlled to a low partial pressure having substantially no effect on detection of NOx.

At the same time, a resulting pump current Ip1 is used to control electromotive force in the main-pump-control oxygen-partial-pressure detection sensor cell 80. Specifically, the pump current Ip1 is input, as a control signal, into the main-pump-control oxygen-partial-pressure detection sensor cell 80, and, through control of the electromotive force V0 thereof, the oxygen partial pressure in the measurement gas introduced through the third diffusion control part 30 into the second internal space 40 is controlled to have a gradient that is always constant. In use as a NOx sensor, the oxygen concentration in the second internal space 40 is maintained to have a constant value of approximately 0.001 ppm by the action of the main pump cell 21 and the auxiliary pump cell 50.

The measurement pump cell 41 detects NOx in the measurement gas in the second internal space 40. The measurement pump cell 41 is an electrochemical pump cell constituted by a NOx measurement electrode (hereinafter, simply referred to as a measurement electrode) 44, the outer pump electrode 23, the second solid electrolyte layer 6, the spacer layer 5, and the first solid electrolyte layer 4. The measurement electrode 44 is provided on an upper surface of a portion of the first solid electrolyte layer 4 facing the second internal space 40 to be separated from the third diffusion control part 30.

The measurement electrode 44 is a porous cermet electrode. The measurement electrode 44 also functions as a NOx reduction catalyst that reduces NOx existing in the atmosphere in the second internal space 40. The measurement electrode 44 is covered with a fourth diffusion control part 45.

The fourth diffusion control part 45 is a film formed of a porous body containing alumina ($Al_2O_3$) as a main component. The fourth diffusion control part 45 plays a role in limiting the amount of NOx flowing into the measurement electrode 44, and also functions as a protective film (measurement electrode protective layer) of the measurement electrode 44.

The measurement pump cell 41 can pump out oxygen generated through decomposition of nitrogen oxides in the atmosphere around the measurement electrode 44, and detect the amount of generated oxygen as a pump current Ip2.

In order to detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an electrochemical sensor cell, namely, a measurement-pump-control oxygen-partial-pressure detection sensor cell 82. A variable power supply 46 is controlled based on electromotive force V2 detected by the measurement-pump-control oxygen-partial-pressure detection sensor cell 82.

The measurement gas introduced into the second internal space 40 reaches the measurement electrode 44 through the fourth diffusion control part 45 under a condition in which the oxygen partial pressure is controlled. Nitrogen oxides in the measurement gas around the measurement electrode 44 are reduced (2 NO→$N_2+O_2$) to generate oxygen. The generated oxygen is pumped by the measurement pump cell 41, and, at that time, a voltage Vp2 of the variable power supply 46 is controlled so that a control voltage V2 detected by the measurement-pump-control oxygen-partial-pressure detection sensor cell 82 is kept constant. The amount of oxygen generated around the measurement electrode 44 is proportional to a nitrogen oxide concentration in the measurement gas, and thus the nitrogen oxide concentration in the measurement gas is calculated using the pump current Ip2 in the measurement pump cell 41.

If the measurement electrode 44, the first solid electrolyte layer 4, the third substrate layer 3, and the reference electrode 42 are combined to constitute an oxygen partial pressure detection means as an electrochemical sensor cell, electromotive force in accordance with a difference between the amount of oxygen generated through reduction of a NOx component in the atmosphere around the measurement electrode 44 and the amount of oxygen contained in reference atmospheric air can be detected, and the concentration of the NOx component in the measurement gas can thereby be obtained.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure in the measurement gas outside the sensor can be detected using electromotive force Vref obtained by the sensor cell 83.

A portion of the sensor element 101 extending from the gas inlet 10 to the second internal space 40 in the longitudinal direction of the element, and further, the electrodes, the pump cells, the sensor cells, and the like provided in the portion, which are described above, relate mainly to measurement of the NOx concentration, and thus they are collectively referred to as a NOx sensor part of the sensor element 101 in the present embodiment.

The sensor element 101 further includes a $NH_3$ sensing electrode (hereinafter, simply referred to as a sensing electrode) 60 on the upper surface of the second solid electrolyte layer 6. The sensing electrode 60 is formed as a porous cermet electrode made of Pt containing a predetermined ratio of Au, namely, a Pt—Au alloy, and zirconia. In the sensor element 101, the sensing electrode 60, the reference electrode 42, and the solid electrolyte layer between the sensing electrode 60 and the reference electrode 42 constitute a mixed potential cell 61. This means that the concentration of $NH_3$ in the measurement gas is obtained using a potential difference occurring due to the difference in $NH_3$ concentration around the sensing electrode 60 and the reference electrode 42 based on the principle of mixed potential. In the present embodiment, portions of the sensor element 101 constituting the mixed potential cell 61 are collectively referred to as a $NH_3$ gas sensor part. The reference electrode 42 is used not only by the $NH_3$ gas sensor part but also by the NOx sensor part as described above, and is thus referred to as a common reference electrode.

Specifically, the catalytic activity of the sensing electrode 60 against a $NH_3$ gas is inactivated in a predetermined concentration range by suitably determining the composition of the Pt—Au alloy being its constituent material. That is, the decomposition reaction of the $NH_3$ gas is prevented or reduced in the sensing electrode 60. Thus, in the gas sensor 100, the potential of the sensing electrode 60 selectively varies with respect to (has correlation with) the $NH_3$ gas in the predetermined concentration range in accordance with the concentration thereof. In other words, the sensing electrode 60 is provided so as to have high concentration dependence of the potential for the $NH_3$ gas in the predetermined concentration range while having low concentration dependence of the potential for other components of the measurement gas.

More specifically, in the sensor element 101, with an Au abundance ratio on the surfaces of Pt—Au alloy particles included in the sensing electrode 60 being suitably determined, the sensing electrode 60 is provided to have noticeable $NH_3$ gas concentration dependence of the potential in a concentration range of 0 ppm to 500 ppm, and at least in a concentration range of 0 ppm to 100 ppm.

In this specification, the Au abundance ratio means an area ratio of a portion covered with Au to a portion at which Pt is exposed in the surface of noble metal particles included in the sensing electrode 60. In this specification, the Au abundance ratio is calculated from an expression shown below using Au and Pt detection values in an Auger spectrum obtained by performing Auger electron spectroscopy (AES) analysis on the surface of the noble metal particles.

$$\text{Au abundance ratio} = \text{Au detection value}/\text{Pt detection value} \quad (1)$$

The Au abundance ratio is one when the area of the portion at which Pt is exposed and the area of the portion covered with Au are equal to each other.

Specifically, the potential of the sensing electrode 60 exhibits noticeable dependence on the $NH_3$ gas concentration in a concentration range of 0 ppm to 500 ppm when the Au abundance ratio of the sensing electrode 60 is equal to or greater than 0.25, and particularly exhibits noticeable dependence on the $NH_3$ gas concentration at least in a concentration range of 0 ppm to 100 ppm when the Au abundance ratio of the sensing electrode 60 is equal to or greater than 0.40. The Au abundance ratio does not have a particular upper limit, and thus the entire surfaces of the noble metal particles included in the sensing electrode 60 may be Au. Alternatively, the sensing electrode 60 may include only Au as the noble metal. When the sensing electrode 60 including the Pt—Au alloy is formed by screen printing and integral firing (co-firing) with the solid electrolyte layers and the electrodes after screen printing as will be described below, the Au abundance ratio is preferably equal to or smaller than 2.30. This is because, if the Au abundance ratio is extremely great, the sensing electrode 10 might unfavorably melt due to lower melting point (1,064° C.) of Au than the firing temperature. The same applies to the sensing electrode 60 including only Au as the noble metal.

The Au abundance ratio can also be calculated using a relative sensitivity coefficient method from a peak intensity of a peak detected for Au and Pt, which is obtained by subjecting the surface of the noble metal particles to X-ray photoelectron spectroscopy (XPS) analysis. The value of the Au abundance ratio obtained by this method can be considered to be substantially the same as the value of the Au abundance ratio calculated based on the result of AES analysis.

The Au abundance ratio expressed by the expression (1) can be considered for an electrode other than the sensing electrode 60. In particular, the inner pump electrode 22 and the auxiliary pump electrode 51 are preferably provided so that the Au abundance ratio is between 0.01 and 0.3 inclusive. In such a case, the catalytic activity of the inner pump electrode 22 and the auxiliary pump electrode 51 is reduced for a substance other than oxygen to increase selective decomposing ability for oxygen. The Au abundance ratio is more preferably 0.1 or more and 0.25 or less, and is much more preferably 0.2 or more and 0.25 or less.

On the other hand, the reference electrode 42 is covered with the atmospheric air introduction layer 48 leading to the reference gas introduction space 43 as described above, and thus the surrounding of the reference electrode 42 is always filled with atmospheric air (oxygen) in use of the gas sensor 100. The reference electrode 42 thus always has a constant potential in use of the gas sensor 100.

Thus, in the mixed potential cell 61, a potential difference EMF occurs between the sensing electrode 60 and the reference electrode 42 in accordance with the concentration of the $NH_3$ gas in the measurement gas at least in a $NH_3$ gas concentration range of 0 ppm to 500 ppm in use of the gas sensor 100.

The sensor element 101 further includes a heater part 70 playing a role in temperature adjustment of heating the sensor element 101 and keeping it warm to enhance the oxygen ion conductivity of the solid electrolyte. The heater part 70 includes a heater electrode 71, a heater 72, a through hole 73, a heater insulating layer 74, and a pressure diffusion hole 75. The heater electrode 71 is an electrode formed to be in contact with a lower surface of the first substrate layer 1.

The heater electrode 71 is to be connected to an external power supply to enable the heater part 70 to be externally powered.

The heater 72 is an electric resistor formed to be vertically sandwiched between the second substrate layer 2 and the third substrate layer 3. The heater 72 is connected to the heater electrode 71 via the through hole 73, and generates heat by being externally powered through the heater electrode 71 to heat the solid electrolytes forming the sensor element 101 and keep it warm.

The heater 72 is buried across the entire region extending from the first internal space 20 to the second internal space 40, and can thereby adjust the sensor element 101 as a whole to a temperature at which the above-mentioned solid electrolyte is activated. The heater insulating layer 74 is an insulating layer formed of an insulator, such as alumina, on upper and lower surfaces of the heater 72. The heater insulating layer 74 is formed for electrical insulation between the second substrate layer 2 and the heater 72 and for electrical insulation between the third substrate layer 3 and the heater 72.

The pressure diffusion hole 75 is a part provided to penetrate the third substrate layer 3 to communicate with the reference gas introduction space 43, and is formed to mitigate an internal pressure rise associated with a temperature rise in the heater insulating layer 74.

In the gas sensor 100, when the NOx concentration is obtained, each part of the sensor element 101 is heated to a temperature suitable for operation and kept warm with the generation of heat in the heater 72. Thus, at the location of each of the pump cells, the sensor cells, and the mixed potential cell 61, they are heated to a temperature suitable for operation. A temperature range suitable for operation, however, differs among them. Specifically, the NOx sensor part (more specifically, a part (a left part in FIG. 1) including the main pump cell 21 including the inner pump electrode 22 and the outer pump electrode 23, and being closer to the distal end portion than the third diffusion control part 30 is) is heated to a predetermined temperature (first temperature) which is 600° C. or higher and 900° C. or lower, and the $NH_3$ gas sensor part (more specifically, the mixed potential cell 61 and a portion around the mixed potential cell 61) is heated to a predetermined temperature (second temperature) which is 400° C. or higher and 650° C. or lower, and is lower than the first temperature.

In the gas sensor 100, the location of each cell, a presence range of the heater, and how to perform heating using the heater 72 are determined to suitably meet these temperature conditions.

Although the sensing electrode 60 is provided on an upper surface of the sensor element 101 (the upper surface of the second solid electrolyte layer 6) and above the reference electrode 42 and the measurement electrode 44 in FIG. 1, the location of the sensing electrode 60 is not limited to this location, and the sensing electrode 60 may be provided on another location on the upper surface of the sensor element 101 as long as the sensing electrode 60 is heated to the above-mentioned second temperature.

The sensor element 101 further includes a surface protective layer 90 located on the upper surface of the second solid electrolyte layer 6 to cover the outer pump electrode 23 and the sensing electrode 60. The surface protective layer 90 is provided for prevention of adhesion of a poisoning substance contained in the measurement gas to the outer pump electrode 23 and the sensing electrode 60. The surface protective layer 90 is preferably formed of porous alumina, for example. The surface protective layer 90 is provided to have a pore diameter and a pore size not controlling gas distribution between the outside of the element and each of the outer pump electrode 23 and the sensing electrode 60.

Operation of each part of the gas sensor 100, for example, application of voltages to the pump cells performed by the variable power supplies and heating performed by the heater 72, is controlled by a controller (controlling means) 110 electrically connected to each part. In addition, the controller 110 determines the NOx concentration in the measurement gas based on the potential difference EMF occurring in the mixed potential cell 61 of the sensor element 101 and the pump current Ip2 flowing through the measurement pump cell 41. The $NH_3$ concentration can be determined in the process of calculating the NOx concentration. This means that the controller 110 functions as a concentration determination means for determining the NOx concentration and further determining the $NH_3$ concentration. Although only a symbol of the potential difference EMF and a symbol of the pump current Ip2 are connected to the controller 110 by arrows in FIG. 1 for clarity of illustration, it is needless to say that other values of the potential difference and values of the pump current are also provided to the controller 110. A general-purpose personal computer is applicable to the controller 110.

<Process of Manufacturing Sensor Element>

The process of manufacturing the sensor element 101 illustrated in FIG. 1 will be described next. Generally speaking, the sensor element 101 illustrated in FIG. 1 is manufactured by forming a laminated body formed of green sheets containing an oxygen-ion conductive solid electrolyte, such as zirconia, as a ceramic component, and by cutting and firing the laminated body. The oxygen-ion conductive solid electrolyte is, for example, yttrium partially stabilized zirconia (YSZ) obtained by internally adding, to zirconia, yttria at a proportion of 3 mol % or more.

Figure 2:
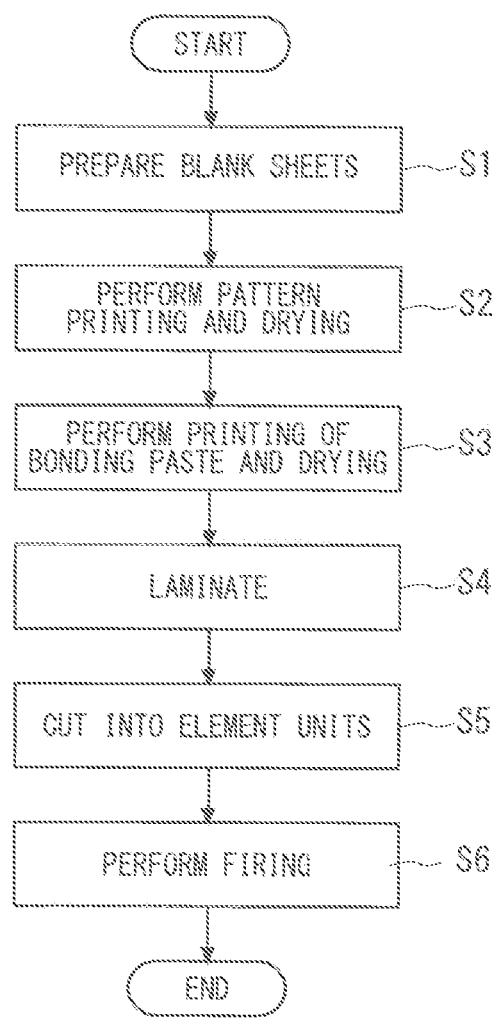
FIG. 2 shows a processing flow in the manufacture of a sensor element 101.

FIG. 2 shows a processing flow in the manufacture of the sensor element 101. In the manufacture of the sensor element 101, blank sheets (not illustrated) that are green sheets having no pattern formed thereon are prepared first (step S1). Specifically, six blank sheets corresponding to the first substrate layer 1, the second substrate layer 2, the third substrate layer 3, the first solid electrolyte layer 4, the spacer layer 5, and the second solid electrolyte layer 6 are prepared. The blank sheets have a plurality of sheet holes used for positioning in printing and lamination. The sheet holes are formed in advance through, for example, punching by a punching machine. Green sheets corresponding to layers forming an internal space also include penetrating portions corresponding to the internal space formed in advance through, for example, punching as described above. The blank sheets corresponding to the respective layers of the sensor element 101 are not required to have the same thickness.

After preparation of the blank sheets corresponding to the respective layers, pattern printing and drying are performed to form various patterns on the individual blank sheets (step S2). Specifically, the electrode patterns of, for example, each pump electrode and the sensing electrode 60, the pattern of the heater 72, the atmospheric air introduction layer 48, internal wiring (not illustrated), and the like are formed. The pattern of the surface protective layer 90 may further be printed. With respect to the first substrate layer 1, a cut mark serving as a reference cut position when the laminated body is cut in a subsequent step is printed.

Each pattern is printed by applying, to the blank sheet, a paste for pattern formation prepared in accordance with the characteristics required for each formation target using a known screen printing technique. Any known drying means is available for drying after printing.

After pattern printing, printing of a bonding paste and drying are performed to laminate and bond the green sheets corresponding to the respective layers (step S3). Any known screen printing technique is available for printing of the bonding paste, and any known drying means is available for drying after printing.

Then, the green sheets to which an adhesive has been applied are stacked in a predetermined order, and the stacked green sheets are crimped on the predetermined temperature and pressure conditions to thereby form a laminated body (step S4). Specifically, crimping is performed by stacking and holding the green sheets as a target of lamination in a predetermined lamination jig (not illustrated) while positioning the green sheets at the sheet holes, and then heating and pressurizing the green sheets together with the lamination jig using a lamination machine, such as a known hydraulic pressing machine. The pressure, temperature, and time for heating and pressurizing depend on a lamination machine to be used, and these conditions may be determined appropriately to achieve good lamination. The surface protective layer 90 may be formed on the laminated body as obtained.

After the laminated body is obtained as described above, the laminated body is cut out at a plurality of positions to obtain individual units (referred to as element bodies) of the sensor element 101 (step S5). The cut out element bodies are fired under predetermined conditions, thereby producing the sensor element 101 as described above (step S6). This means that the sensor element 101 is produced by integral firing (co-firing) of the solid electrolyte layers and the electrodes. The firing temperature is preferably 1,200° C. or higher and 1,500° C. or lower (e.g., 1,400° C.). Integral firing performed in such a manner provides sufficient adhesion strength to each of the electrodes of the sensor element 101. This contributes to improvement in durability of the sensor element 101.

The sensor element 101 thus obtained is housed in a predetermined housing, and incorporated into a main body (not illustrated) of the gas sensor 100.

<Determination of NOx Concentration in Presence of $NH_3$ Gas>

When the gas sensor 100 having the configuration as described above is used to obtain the NOx concentration in the measurement gas, the gas sensor 100 is located so that one end portion of the sensor element 101 having a predetermined range from the gas inlet 10 at least including the sensing electrode 60 is located in a measurement gas atmosphere, and the other end portion is located not to be in contact with the measurement gas atmosphere. With operation of the main pump cell 21 and the auxiliary pump cell 50 while being heated by the heater 72, the measurement gas whose oxygen partial pressure always maintained in a constant low value (value having substantially no effect on NOx measurement) is supplied to the measurement pump cell 41. The NOx concentration in the measurement gas can be obtained based on the fact that the pump current Ip2, flowing when the measurement pump cell 41 pumps out oxygen generated through NOx reduction at the measurement electrode 44, is approximately proportional to the NOx concentration in the measurement gas.

However, as also mentioned in Japanese Patent No. 5209401 and Japanese Patent Application Laid-Open Publication No. 2015-034814, for example, the value of the pump current Ip2 varies depending on the concentration of the $NH_3$ gas when the $NH_3$ gas is intermingled in the measurement gas.

FIG. 3 illustrates gas concentration dependence of the pump current Ip2 when the $NH_3$ gas and NOx coexist. Specifically, FIG. 3 is obtained by plotting, with respect to the $NH_3$ gas concentration, values obtained by the gas sensor 100 having the configuration illustrated in FIG. 1 through measurement of the pump current Ip2 targeted at 36 model gases corresponding to different combinations of six levels of the $NH_3$ gas concentration and six levels of the NO gas concentration under conditions shown below. The Au abundance ratio of the sensing electrode 60 and the Au abundance ratio of the outer pump electrode 23 are each set to 0.36. On the other hand, the Au abundance ratio of the inner pump electrode 22 and the Au abundance ratio of the auxiliary pump electrode 51 are each set to 0.22.

[Model Gas Conditions]
Flow rate: 5 L/min;
Gas temperature: 120° C.; and
Gas composition:
$NH_3$=0 ppm, 100 ppm, 200 ppm, 300 ppm, 400 ppm, or 500 ppm;
NO=0 ppm, 100 ppm, 200 ppm, 300 ppm, 400 ppm, or 500 ppm;
$O_2$=10%;
$H_2O$=5%; and
$N_2$=balance.

It can be seen from FIG. 3 that the pump current Ip2 varies depending on the $NH_3$ gas concentration even if the NO concentration is constant, and the pump current Ip2 linearly varies depending on the $NH_3$ gas concentration when the NO concentration is constant. In a case where the pump current Ip2 is 1.5 µA, for example, the NO concentration is approximately 500 ppm when the $NH_3$ gas concentration is 100 ppm, whereas the NO concentration is approximately 100 ppm when the $NH_3$ gas concentration is 400 ppm.

This means that, when NOx and the $NH_3$ gas coexist in the measurement gas, the NOx concentration cannot be determined with high precision only by measuring the pump current Ip2, and applying a value obtained through measurement to a functional relationship expressing the relationship between the pump current Ip2 and the NOx concentration.

The gas sensor 100 according to the present embodiment solves this problem by using the potential difference occurring between the sensing electrode 60 and the reference electrode 42 in the mixed potential cell 61.

FIG. 4 is a diagram obtained by plotting, with respect to the $NH_3$ gas concentration, values of the potential difference EMF occurring in the mixed potential cell 61 measured at the same time as measurement of the pump current Ip2 shown in FIG. 3. In other words, FIG. 4 illustrates gas concentration dependence of the potential difference EMF when the $NH_3$ gas and NOx coexist.

As can be seen from FIG. 4, there is no difference in the dependence of the potential difference EMF on the $NH_3$ gas concentration with regard to the NO concentration. This means that the value of the potential difference EMF obtained in the mixed potential cell 61 is not interfered with the NOx concentration, in other words, the $NH_3$ gas concentration in the measurement gas can be determined based on the value of the potential difference EMF once the potential difference EMF is obtained.

In view of these findings, the gas sensor 100 according to the present embodiment uses not only the value of the pump current Ip2 but also the $NH_3$ gas concentration determined based on the potential difference EMF in the determination of the NOx concentration in the measurement gas.

For example, processing is performed in accordance with procedures as described below. The NOx concentration can thus be obtained with high precision even when the $NH_3$ gas is intermingled in the measurement gas.

(1) Preparing in advance a NOx concentration map (FIG. 3 shows an example thereof) indicating the relationship among the $NH_3$ gas concentration, the NOx concentration, and the pump current Ip2, and a $NH_3$ concentration map (FIG. 4 shows an example thereof) indicating the relationship between the potential difference EMF occurring in the mixed potential cell 61 and the $NH_3$ gas concentration, using a plurality of model gases of known concentrations corresponding to different combinations of the NOx concentration and the $NH_3$ gas concentration as in the above-mentioned example, and storing the NOx concentration map and the $NH_3$ concentration map in the controller 110, which is a concentration determination means.

(2) In actual use of the gas sensor 100, acquiring, at the controller 110, the value of the potential difference EMF occurring in the mixed potential cell 61 and the value of the pump current Ip2 flowing through the measurement pump cell 41 at an appropriate timing.

(3) Determining the $NH_3$ gas concentration by collating, at the controller 110, the value of the potential difference EMF as acquired with the $NH_3$ concentration map.

(4) Then determining the NOx concentration by collating the value of the pump current Ip2 and the $NH_3$ gas concentration as determined previously with the NOx concentration map.

(5) Repeating the procedures (2) to (4) in the case of continuously obtaining the NOx concentration.

While the above-mentioned processing is intended to obtain the NOx concentration with improved precision, in the middle of processing, the $NH_3$ gas concentration is inevitably determined using the $NH_3$ concentration map, and besides, the $NH_3$ gas concentration is not interfered with NOx as described above. It can thus be said that the gas sensor 100 according to the present embodiment can obtain NOx and the $NH_3$ gas in the measurement gas concurrently and in parallel to each other with high precision.

In the gas sensor 100 according to the present embodiment, the measurement pump cell 41 through which the pump current Ip2 flows and the mixed potential cell 61 in which the potential difference EMF occurs share the reference electrode 42 located inside the atmospheric air introduction layer 48 and being in contact with atmospheric air always having a constant oxygen concentration. Thus, both of the oxygen pump current Ip2 and the potential difference EMF are obtained with stability. This also contributes to improvement in precision in determining the NOx concentration and the $NH_3$ gas concentration.

Since the measurement pump cell 41 and the mixed potential cell 61 share the reference electrode 42, simplified internal configuration of the sensor element 101 and space-saving are achieved compared with a conventional multi-gas sensor in which these cells have respective reference electrodes.

As described above, the present embodiment enables the gas sensor to obtain the NOx concentration with stability and high precision even when NOx and the $NH_3$ gas coexist in the measurement gas and to further concurrently obtain the $NH_3$ gas concentration with stability and high precision. In addition, the gas sensor has simplified configuration compared with a conventional multi-gas sensor.

<Modifications>

In the above-mentioned embodiment, the NOx concentration map indicating the relationship among the $NH_3$ gas concentration, the NOx concentration, and the pump current Ip2, and the $NH_3$ concentration map indicating the relationship between the potential difference EMF occurring in the mixed potential cell 61 and the $NH_3$ gas concentration are prepared, and the $NH_3$ gas concentration determined based on the $NH_3$ concentration map is applied to the NOx concentration map to determine the NOx concentration, but the $NH_3$ gas concentration may not be calculated to determine the NOx concentration.

For example, the NOx concentration map may be prepared to indicate the relationship among the potential difference EMF occurring in the mixed potential cell 61, the NOx concentration, and the pump current Ip2, and the controller 110 may collate the value of the potential difference EMF occurring in the mixed potential cell 61 and the value of the pump current Ip2 flowing through the measurement pump cell 41 with the NOx concentration map, thereby determining the NOx concentration. Also in this case, the $NH_3$ gas concentration may naturally be determined using the $NH_3$ concentration map.

In the above-mentioned embodiment, the sensor element 101 has two internal spaces, namely, the first internal space 20 and the second internal space 40, but the sensor element 101 is not limited to have such configuration. For example, a third internal space communicating with the second internal space 40 may be provided, and the measurement electrode 44 may be provided inside the third internal space in place of the second internal space 40. In this case, the fourth diffusion control part 45 covering the measurement electrode 44 may be omitted by serving a part at which the second internal space 40 and the third internal space communicate with each other as the diffusion control part.

As described above, the Au abundance ratio is preferably equal to or smaller than 2.30 in view of the melting point of Au when the sensing electrode 60 including the Pt—Au alloy is formed by screen printing and co-firing, but, if the sensing electrode 60 is formed by other methods, the sensing electrode 60 including the Pt—Au alloy and having an Au abundance ratio greater than 2.30 or the sensing electrode 60 including Au can be formed. Specifically, a method of manufacturing a laminated body and further the fired body therefrom without formation of the sensing electrode, and then forming the sensing electrode 60 with respect to the fired body is considered. For example, so-called secondary firing that is a method of forming the pattern of the sensing electrode by screen printing and then performing firing again or a method of forming the sensing electrode by plating may be used.

While the invention has been shown and described in detail, the foregoing description is in all aspects illustrative and not restrictive. It is therefore understood that numerous modifications and variations can be devised without departing from the scope of the invention.

What is claimed is:

1. A gas sensor for detecting a plurality of predetermined gas components in a measurement gas, said gas sensor comprising:
   a sensor element including a lamination of a plurality of oxygen-ion conductive solid electrolyte layers, wherein said sensor element includes:
      a NOx sensor part;
      a $NH_3$ gas sensor part; and
      a single common reference electrode shared by said NOx sensor part and said $NH_3$ gas sensor part, said NOx sensor part includes:
      at least one internal space into which said measurement gas is introduced from an external space;
      a NOx measurement electrode formed to face said at least one internal space; and
      an outer pump electrode formed on a surface of said sensor element, and
      a measurement pump cell that is an electrochemical pump cell constituted by said NOx measurement electrode, said outer pump electrode, and a solid electrolyte between said NOx measurement electrode and said outer pump electrode, which is a first part of said plurality of oxygen-ion conductive solid electrolyte layers,
   said $NH_3$ gas sensor part includes a $NH_3$ sensing electrode formed on a surface of said sensor element and having catalytic activity inactivated for a $NH_3$ gas,
   said single common reference electrode is located between two of said plurality of oxygen-ion conductive solid electrolyte layers to be in contact with a reference gas,
   said $NH_3$ sensing electrode, said common reference electrode, and a solid electrolyte between said $NH_3$ sensing electrode and said common reference electrode, which is a second part of said plurality of oxygen-ion conductive solid electrolyte layers, constitute a mixed potential cell, and
   said gas sensor is configured to determine a NOx concentration in said measurement gas based on:
      a potential difference occurring between said $NH_3$ sensing electrode and said common reference electrode in said mixed potential cell; and
      a pump current flowing between said NOx measurement electrode and said outer pump electrode in a state of controlling a voltage applied across said NOx measurement electrode and said outer pump electrode to maintain a potential difference between said NOx measurement electrode and said common reference electrode constant.

2. The gas sensor according to claim 1, wherein said gas sensor is configured to determine a $NH_3$ gas concentration in said measurement gas based on said potential difference occurring between said $NH_3$ sensing electrode and said common reference electrode in said mixed potential cell.

3. The gas sensor according to claim 2, wherein said gas sensor is configured to determine said NOx concentration in said measurement gas based on said $NH_3$ gas concentration in said measurement gas determined in said mixed potential cell and said pump current.

4. The gas sensor according to claim 1, further comprising a heater located inside said sensor element to heat said sensor element,
   wherein said heater is configured to heat said NOx sensor part to a first temperature which is 600° C. or higher and 900° C. or lower, and heat said $NH_3$ gas sensor part to a second temperature which is 400° C. or higher and 650° C. or lower, and is lower than said first temperature.

5. The gas sensor according to claim 1, wherein said sensing electrode is formed of a cermet composed of a noble metal and an oxygen-ion conductive solid electrolyte,
   said noble metal is a Pt—Au alloy or Au, and
   an Au abundance ratio is equal to or greater than 0.25 when said noble metal is said Pt—Au alloy, said Au abundance ratio being an area ratio of a portion covered with Au to a portion at which Pt is exposed in a surface of noble metal particles included in said sensing electrode.

6. The gas sensor according to claim 1, wherein
said at least one internal space comprises a first internal space and a second internal space,
said NOx measurement electrode is located inside said second internal space, and has NOx reducing ability,
said sensor element further includes:
  a gas inlet through which said measurement gas is introduced from said external space into said sensor element;
  an inner pump electrode formed to face said first internal space; and
  an auxiliary pump electrode formed to face said second internal space,
said gas inlet and said first internal space, and said first internal space and said second internal space each communicate with each other via a diffusion control part providing a predetermined diffusion resistance to said measurement gas,
said inner pump electrode, said outer pump electrode, and a solid electrolyte between said inner pump electrode and said outer pump electrode, which is a third part of said plurality of oxygen-ion conductive solid electrolyte layers, constitute a main pump cell pumping in or pumping out oxygen between said first internal space and said external space,
said auxiliary pump electrode, said outer pump electrode, and a solid electrolyte between said auxiliary pump electrode and said outer pump electrode, which is a fourth part of said plurality of oxygen-ion conductive solid electrolyte layers, constitute an auxiliary pump cell that is an electrochemical pump cell pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

7. The gas sensor according to claim 2, further comprising a heater located inside said sensor element to heat said sensor element,
wherein said heater is configured to heat said NOx sensor part to a first temperature which is 600° C. or higher and 900° C. or lower, and heat said $NH_3$ gas sensor part to a second temperature which is 400° C. or higher and 650° C. or lower, and is lower than said first temperature.

8. The gas sensor according to claim 3, further comprising a heater located inside said sensor element to heat said sensor element,
wherein said heater is configured to heat said NOx sensor part to a first temperature which is 600° C. or higher and 900° C. or lower, and heat said $NH_3$ gas sensor part to a second temperature which is 400° C. or higher and 650° C. or lower, and is lower than said first temperature.

9. The gas sensor according to claim 2, wherein
said sensing electrode is formed of a cermet composed of a noble metal and an oxygen-ion conductive solid electrolyte,
said noble metal is a Pt—Au alloy or Au, and
an Au abundance ratio is equal to or greater than 0.25 when said noble metal is said Pt—Au alloy, said Au abundance ratio being an area ratio of a portion covered with Au to a portion at which Pt is exposed in a surface of noble metal particles included in said sensing electrode.

10. The gas sensor according to claim 3, wherein
said sensing electrode is formed of a cermet composed of a noble metal and an oxygen-ion conductive solid electrolyte,
said noble metal is a Pt—Au alloy or Au, and
an Au abundance ratio is equal to or greater than 0.25 when said noble metal is said Pt—Au alloy, said Au abundance ratio being an area ratio of a portion covered with Au to a portion at which Pt is exposed in a surface of noble metal particles included in said sensing electrode.

11. The gas sensor according to claim 4, wherein
said sensing electrode is formed of a cermet composed of a noble metal and an oxygen-ion conductive solid electrolyte,
said noble metal is a Pt—Au alloy or Au, and
an Au abundance ratio is equal to or greater than 0.25 when said noble metal is said Pt—Au alloy, said Au abundance ratio being an area ratio of a portion covered with Au to a portion at which Pt is exposed in a surface of noble metal particles included in said sensing electrode.

12. The gas sensor according to claim 7, wherein
said sensing electrode is formed of a cermet composed of a noble metal and an oxygen-ion conductive solid electrolyte,
said noble metal is a Pt—Au alloy or Au, and
an Au abundance ratio is equal to or greater than 0.25 when said noble metal is said Pt—Au alloy, said Au abundance ratio being an area ratio of a portion covered with Au to a portion at which Pt is exposed in a surface of noble metal particles included in said sensing electrode.

13. The gas sensor according to claim 8, wherein
said sensing electrode is formed of a cermet composed of a noble metal and an oxygen-ion conductive solid electrolyte,
said noble metal is a Pt—Au alloy or Au, and
an Au abundance ratio is equal to or greater than 0.25 when said noble metal is said Pt—Au alloy, said Au abundance ratio being an area ratio of a portion covered with Au to a portion at which Pt is exposed in a surface of noble metal particles included in said sensing electrode.

14. The gas sensor according to claim 2, wherein
said at least one internal space comprises a first internal space and a second internal space,
said NOx measurement electrode is located inside said second internal space, and has NOx reducing ability,
said sensor element further includes:
  a gas inlet through which said measurement gas is introduced from said external space into said sensor element;
  an inner pump electrode formed to face said first internal space; and
  an auxiliary pump electrode formed to face said second internal space,
said gas inlet and said first internal space, and said first internal space and said second internal space each communicate with each other via a diffusion control part providing a predetermined diffusion resistance to said measurement gas, said inner pump electrode, said outer pump electrode, and a solid electrolyte between said inner pump electrode and said outer pump electrode, which is a third part of said plurality of oxygen-ion conductive solid electrolyte layers, constitute a main pump cell pumping in or pumping out oxygen between said first internal space and said external space, said auxiliary pump electrode, said outer pump electrode, and a solid electrolyte between said auxiliary pump electrode and said outer pump electrode, which is a fourth part of said plurality of oxygen-ion conductive solid electrolyte layers, constitute an auxiliary pump cell that is an electrochemical pump cell pumping out oxygen from said second internal space to said external space, and said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

15. The gas sensor according to claim 3, wherein
said at least one internal space comprises a first internal space and a second internal space,
said NOx measurement electrode is located inside said second internal space, and has NOx reducing ability,
said sensor element further includes:
  a gas inlet through which said measurement gas is introduced from said external space into said sensor element;
  an inner pump electrode formed to face said first internal space; and
  an auxiliary pump electrode formed to face said second internal space,
said gas inlet and said first internal space, and said first internal space and said second internal space each communicate with each other via a diffusion control part providing a predetermined diffusion resistance to said measurement gas,
said inner pump electrode, said outer pump electrode, and a solid electrolyte between said inner pump electrode and said outer pump electrode, which is a third part of said plurality of oxygen-ion conductive solid electrolyte layers, constitute a main pump cell pumping in or pumping out oxygen between said first internal space and said external space,
said auxiliary pump electrode, said outer pump electrode, and a solid electrolyte between said auxiliary pump electrode and said outer pump electrode, which is a fourth part of said plurality of oxygen-ion conductive solid electrolyte layers, constitute an auxiliary pump cell that is an electrochemical pump cell pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

16. The gas sensor according to claim 4, wherein
said at least one internal space comprises a first internal space and a second internal space,
said NOx measurement electrode is located inside said second internal space, and has NOx reducing ability,
said sensor element further includes:
  a gas inlet through which said measurement gas is introduced from said external space into said sensor element;
  an inner pump electrode formed to face said first internal space; and
  an auxiliary pump electrode formed to face said second internal space,
said gas inlet and said first internal space, and said first internal space and said second internal space each communicate with each other via a diffusion control part providing a predetermined diffusion resistance to said measurement gas,
said inner pump electrode, said outer pump electrode, and a solid electrolyte between said inner pump electrode and said outer pump electrode, which is a third part of said plurality of oxygen-ion conductive solid electrolyte layers, constitute a main pump cell pumping in or pumping out oxygen between said first internal space and said external space,
said auxiliary pump electrode, said outer pump electrode, and a solid electrolyte between said auxiliary pump electrode and said outer pump electrode, which is a fourth part of said plurality of oxygen-ion conductive solid electrolyte layers, constitute an auxiliary pump cell that is an electrochemical pump cell pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

17. The gas sensor according to claim 5, wherein
said at least one internal space comprises a first internal space and a second internal space,
said NOx measurement electrode is located inside said second internal space, and has NOx reducing ability,
said sensor element further includes:
  a gas inlet through which said measurement gas is introduced from said external space into said sensor element;
  an inner pump electrode formed to face said first internal space; and
  an auxiliary pump electrode formed to face said second internal space,
said gas inlet and said first internal space, and said first internal space and said second internal space each communicate with each other via a diffusion control part providing a predetermined diffusion resistance to said measurement gas,
said inner pump electrode, said outer pump electrode, and a solid electrolyte between said inner pump electrode and said outer pump electrode, which is a third part of said plurality of oxygen-ion conductive solid electrolyte layers, constitute a main pump cell pumping in or pumping out oxygen between said first internal space and said external space,
said auxiliary pump electrode, said outer pump electrode, and a solid electrolyte between said auxiliary pump electrode and said outer pump electrode, which is a fourth part of said plurality of oxygen-ion conductive solid electrolyte layers, constitute an auxiliary pump cell that is an electrochemical pump cell pumping out oxygen from said second internal space to said external space, and said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

18. The gas sensor according to claim 7, wherein
said at least one internal space comprises a first internal space and a second internal space,
said NOx measurement electrode is located inside said second internal space, and has NOx reducing ability,
said sensor element further includes:
  a gas inlet through which said measurement gas is introduced from said external space into said sensor element;
  an inner pump electrode formed to face said first internal space; and
  an auxiliary pump electrode formed to face said second internal space,
said gas inlet and said first internal space, and said first internal space and said second internal space each communicate with each other via a diffusion control part providing a predetermined diffusion resistance to said measurement gas,
said inner pump electrode, said outer pump electrode, and a solid electrolyte between said inner pump electrode and said outer pump electrode, which is a third part of said plurality of oxygen-ion conductive solid electrolyte layers, constitute a main pump cell pumping in or pumping out oxygen between said first internal space and said external space,
said auxiliary pump electrode, said outer pump electrode, and a solid electrolyte between said auxiliary pump electrode and said outer pump electrode, which is a fourth part of said plurality of oxygen-ion conductive solid electrolyte layers, constitute an auxiliary pump cell that is an electrochemical pump cell pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

19. The gas sensor according to claim 8, wherein
said at least one internal space comprises a first internal space and a second internal space,
said NOx measurement electrode is located inside said second internal space, and has NOx reducing ability,
said sensor element further includes:
  a gas inlet through which said measurement gas is introduced from said external space into said sensor element;
  an inner pump electrode formed to face said first internal space; and
  an auxiliary pump electrode formed to face said second internal space,
said gas inlet and said first internal space, and said first internal space and said second internal space each communicate with each other via a diffusion control part providing a predetermined diffusion resistance to said measurement gas,
said inner pump electrode, said outer pump electrode, and an oxygen-ion conductive solid electrolyte layer between said inner pump electrode and said outer pump electrode constitute a main pump cell pumping in or pumping out oxygen between said first internal space and said external space,
said auxiliary pump electrode, said outer pump electrode, and an oxygen-ion conductive solid electrolyte layer between said auxiliary pump electrode and said outer pump electrode constitute an auxiliary pump cell that is an electrochemical pump cell pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

20. The gas sensor according to claim 9, wherein
said at least one internal space comprises a first internal space and a second internal space,
said NOx measurement electrode is located inside said second internal space, and has NOx reducing ability,
said sensor element further includes:
  a gas inlet through which said measurement gas is introduced from said external space into said sensor element;
  an inner pump electrode formed to face said first internal space; and
  an auxiliary pump electrode formed to face said second internal space,
said gas inlet and said first internal space, and said first internal space and said second internal space each communicate with each other via a diffusion control part providing a predetermined diffusion resistance to said measurement gas,
said inner pump electrode, said outer pump electrode, and a solid electrolyte between said inner pump electrode and said outer pump electrode, which is a third part of said plurality of oxygen-ion conductive solid electrolyte layers, constitute a main pump cell pumping in or pumping out oxygen between said first internal space and said external space,
said auxiliary pump electrode, said outer pump electrode, and a solid electrolyte between said auxiliary pump electrode and said outer pump electrode, which is a fourth part of said plurality of oxygen-ion conductive solid electrolyte layers, constitute an auxiliary pump cell that is an electrochemical pump cell pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

21. A gas sensor for detecting a plurality of predetermined gas components in a measurement gas, said gas sensor comprising:
  a sensor element including a lamination of a plurality of oxygen-ion conductive solid electrolyte layers, wherein
  said sensor element includes:
    a NOx sensor part;
    a $NH_3$ gas sensor part; and
    a common reference electrode shared by said NOx sensor part and said $NH_3$ gas sensor part,
  said NOx sensor part includes:
    at least one internal space into which said measurement gas is introduced from an external space;
    a NOx measurement electrode formed to face said at least one internal space; and
    an outer pump electrode formed on a surface of said sensor element,
  said $NH_3$ gas sensor part includes a $NH_3$ sensing electrode formed on a surface of said sensor element and having catalytic activity inactivated for a $NH_3$ gas,
  said common reference electrode is located between two of said plurality of oxygen-ion conductive solid electrolyte layers to be in contact with a reference gas,
  said $NH_3$ sensing electrode, said common reference electrode, and a solid electrolyte between said $NH_3$ sensing electrode and said common reference electrode, which is a first part of said plurality of oxygen-ion conductive solid electrolyte layers, form a mixed potential cell, and
  said gas sensor is configured to determine a NOx concentration in said measurement gas based on:
    a potential difference occurring between said $NH_3$ sensing electrode and said common reference electrode in said mixed potential cell; and
    a pump current flowing between said NOx measurement electrode and said outer pump electrode in a state of controlling a voltage applied across said NOx measurement electrode and said outer pump electrode to maintain a potential difference between said NOx measurement electrode and said common reference electrode constant.

* * * * *